US012697133B2

(12) United States Patent
Rizik et al.

(10) Patent No.: US 12,697,133 B2
(45) Date of Patent: Aug. 4, 2026

(54) SYSTEM FOR INCISING LEAFLETS OF A HEART VALVE

(71) Applicant: Bedrosian Global, LLC, Scottsdale, AZ (US)

(72) Inventors: David Rizik, Scottsdale, AZ (US); Bert Bedrosian, Beverly Hills, CA (US)

(73) Assignee: BEDROSIAN GLOBAL, LLC, Scottsdale, AZ (US)

( * ) Notice: Subject to any disclaimer, the term of this patent is extended or adjusted under 35 U.S.C. 154(b) by 570 days.

(21) Appl. No.: 17/989,105

(22) Filed: Nov. 17, 2022

(65) Prior Publication Data

US 2023/0149038 A1     May 18, 2023

Related U.S. Application Data

(60) Provisional application No. 63/280,501, filed on Nov. 17, 2021.

(51) Int. Cl.
*A61B 17/3207* (2006.01)
*A61B 17/22* (2006.01)
*A61B 18/00* (2006.01)

(52) U.S. Cl.
CPC ................. *A61B 17/320725* (2013.01); *A61B 2017/22061* (2013.01); *A61B 2018/00369* (2013.01); *A61B 2018/00601* (2013.01)

(58) Field of Classification Search
CPC .. A61B 17/320725; A61B 2017/22097; A61B 2017/320791; A61B 2018/00214; A61B 2018/0022; A61B 2018/00369; A61B 2018/00601; A61B 17/22012; A61B 2017/22061; A61M 25/104; A61M 2025/1086
See application file for complete search history.

(56) References Cited

U.S. PATENT DOCUMENTS

| | | | |
|---|---|---|---|
| 6,258,108 B1 * | 7/2001 | Lary | .............. A61B 17/320725 |
| | | | 606/159 |
| 2013/0041391 A1 | 2/2013 | Spencer | |
| 2013/0116715 A1 * | 5/2013 | Weber | .................... A61F 2/014 |
| | | | 606/159 |
| 2016/0120565 A1 | 5/2016 | Kobayashi | |
| 2016/0317288 A1 * | 11/2016 | Rogers | .................. A61F 2/2436 |
| 2018/0228537 A1 * | 8/2018 | Dong | ........................ A61F 2/90 |

(Continued)

FOREIGN PATENT DOCUMENTS

| | | | | |
|---|---|---|---|---|
| WO | WO-2021009063 A1 * | 1/2021 | ....... | A61B 17/00234 |
| WO | WO-2021188609 A2 * | 9/2021 | ..... | A61B 17/320016 |

OTHER PUBLICATIONS

International Search Report and Written Opinion issued in PCT/US22/50235.

*Primary Examiner* — Diane D Yabut
*Assistant Examiner* — Christian D Knauss
(74) *Attorney, Agent, or Firm* — Jeffer Mangels & Mitchell LLP; Brennan C. Swain, Esq.

(57) ABSTRACT

A cutting system for use prior to valve replacement that includes a cutting assembly and a sheath. The cutting assembly includes an expansion member that is movable between a stowed position and an expanded position, and at least a first cutting member associated with the expansion member. The first cutting member is configured to incise a first leaflet. The sheath defines a lumen therethrough and the cutting assembly is movable within the lumen.

15 Claims, 10 Drawing Sheets

(56) References Cited

U.S. PATENT DOCUMENTS

| | | | |
|---|---|---|---|
| 2019/0298517 A1 | 10/2019 | Sanchez | |
| 2020/0289102 A1* | 9/2020 | Wilson | ........... A61B 17/320016 |
| 2021/0145561 A1 | 5/2021 | Rizik | |

* cited by examiner

10

SYSTEM FOR INCISING LEAFLETS OF A HEART VALVE

CROSS REFERENCE TO RELATED APPLICATIONS

This application claims the benefit of U.S. Provisional Application No. 63/280,501, filed Nov. 17, 2021, the entirety of which is incorporated by reference herein.

FIELD OF THE INVENTION

The present invention relates generally to a device or assembly for incising the leaflets of a heart valve.

BACKGROUND OF THE INVENTION

Transcatheter aortic valve replacement (TAVR) has become increasingly popular for replacing native heart valves in recent years. Surgical replacement of the aortic valve is also known. Obstruction of the coronary arteries by the native leaflets is a concern during performance of a valve replacement procedure. Obstruction of the coronary arteries by the leaflets of a first replacement valve is also a concern during a second or valve in valve TAVR procedure. Occlusion, jailing off or incarceration of the coronary arteries during or after the valve replacement procedure can be catastrophic.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a cutting system for use prior to valve replacement. The cutting assembly includes a cutting assembly that includes an expansion member that is movable between a stowed position and an expanded position, and at least a first cutting member associated with the expansion member. The first cutting member is configured to incise a first leaflet. In a preferred embodiment, the first cutting member is sharpened such that it cuts or incises the first leaflet when deployed. The cutting system also includes a sheath that defines a lumen therethrough and the cutting assembly is movable within the lumen. In a preferred embodiment, the first cutting member extends outwardly from the expansion member. In a preferred embodiment, the first cutting member includes an actuated state in which the first cutting member is electrified. The expansion member may be an expandable frame that is biased to the expanded position. The expansion member may be an expandable balloon.

In a preferred embodiment, the cutting assembly includes second and third cutting members associated with the expansion member. The second and third cutting members are configured to incise second and third leaflets, respectively. The first, second and third cutting members define a length dimension, and the length dimension is greater than a leaflet, cage or replacement valve length.

In a preferred embodiment, the expansion member is movable from the stowed position to an intermediate position and from the intermediate position to the expanded position. The cutting system may include a switch member that is configured to move the expansion member from the intermediate position to the expanded position. The switch member is preferably movable between a first position and a second position. Movement of the switch member from the first position to the second position moves the expansion member from the intermediate position to the expanded position.

In a preferred embodiment, the cutting assembly includes at least a first arm that is movable between a first position and a second position. the first arm may be embedded or otherwise incorporated into the expansion member or the frame thereof. Movement of the first arm from the first position to the second position moves the expansion member from the intermediate position to the expanded position.

In a preferred embodiment, the first cutting member may be movable with respect to the expansion member between a non-cutting position and a cutting position. Preferably, the cutting system includes a switch member that is configured to move the first cutting member from the non-cutting position to the cutting position.

In accordance with another aspect of the present invention, a method of preparing a heart valve for transcatheter valve replacement is provided. The method includes delivering a cutting assembly to a valve site, expanding an expansion member that includes at least a first cutting member associated therewith, and incising the leaflet. The heart valve may be a native heart valve or a replacement valve. The leaflet may be incised via a cutting surface and/or via an electrified surface. The method may include moving the first cutting member with respect to the expansion member and/or within a slot in the expansion member. The movement may be axial, radial, outward, longitudinal, helical, lateral or any other desired direction.

Generally, the present invention is a cutting system that includes a cutting assembly having an expansion member with cutting members extending radially outwardly therefrom. The cutting members may be electrified so that when the expansion member is deployed or expanded into the leaflets, the leaflets are cut by one or both of the sharp cutting edge of the cutting member and the electrification. The cutting system may include any number of cutting members. In a preferred embodiment, the cutting assembly includes three cutting members, one for cutting each of the three leaflets of the aortic valve or replacement aortic valve. In another preferred embodiment, the cutting assembly includes two cutting members for providing protection for the coronary arteries. In another preferred embodiment, the cutting assembly includes more than three cutting members so that each leaflet is cut in more than one location. The device can also be used in other structures, areas or anatomy where cutting or incising may be useful or necessary. For example, the cutting system or assembly can be used in the mitral valve. In another embodiment, the cutting members can extend in a direction other than longitudinally or parallel to the axis of the catheter or delivery member. For example, the cutting members can extend perpendicular to the axis or at an angle between 0° and 90°. The cutting members can be angled differently. The cutting members can be non-straight, zig-zagged, curved or any other arrangement or orientation depending on the structure or anatomy to be cut or incised. U.S. Patent Publication No. 2019/0298517 is incorporated by reference herein in its entirety.

The cutting assembly can include a handle assembly or control assembly for controlling the various actions of the components positioned distally and/or within the heart during use. For example, the control assembly can include one or more actuators to individually or collectively control proximal and/or distal movement of the components, electrification of the cutting members, expansion of the expansion member or the like. It will be appreciated that only a portion of the catheter/sheath, expansion members, guide wire and other components are shown and that these components can extend as far as needed to enable transcatheter delivery of the components to a valve while allowing the control or handle assembly to remain exterior of the patient for use by a user. The cutting assembly may include an inner catheter for pushing and/or pulling of the expansion member and components, for delivery to the valve or work site, for movement of the cutting members as desired and for retraction of the components. Shockwave lithotripsy may also be incorporated into the present invention.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
FIG. 1 is a perspective view of a cutting assembly positioned within an aorta and prior to cutting of a first replacement heart valve in accordance with a preferred embodiment of the present invention.
Figure 1:

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the—disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

The present invention is a system for splitting, cutting, incising or otherwise affecting the leaflet(s) of a heart valve (whether it be a native leaflet or the leaflet of an already inserted replacement valve) in two (or more pieces) so that it cannot block the coronary artery once it has been pushed aside by a replacement heart valve assembly. Generally, the leaflet cutting system 10 includes a cutting assembly 12 that is delivered via a sheath or catheter 14 and over a guidewire 16. The cutting assembly 12 includes an expansion member 18 having one or more blades, microtomes or cutting members 20 thereon. In a preferred embodiment, the expansion member 18 is a stent, frame, braid frame or the like that automatically expands upon removal from the lumen 15 of the catheter 14 and that includes an outer surface 18a on which the cutting members 20 are positioned. The braided frame provides needed radial strength for the cutting procedure.

Figure 6:
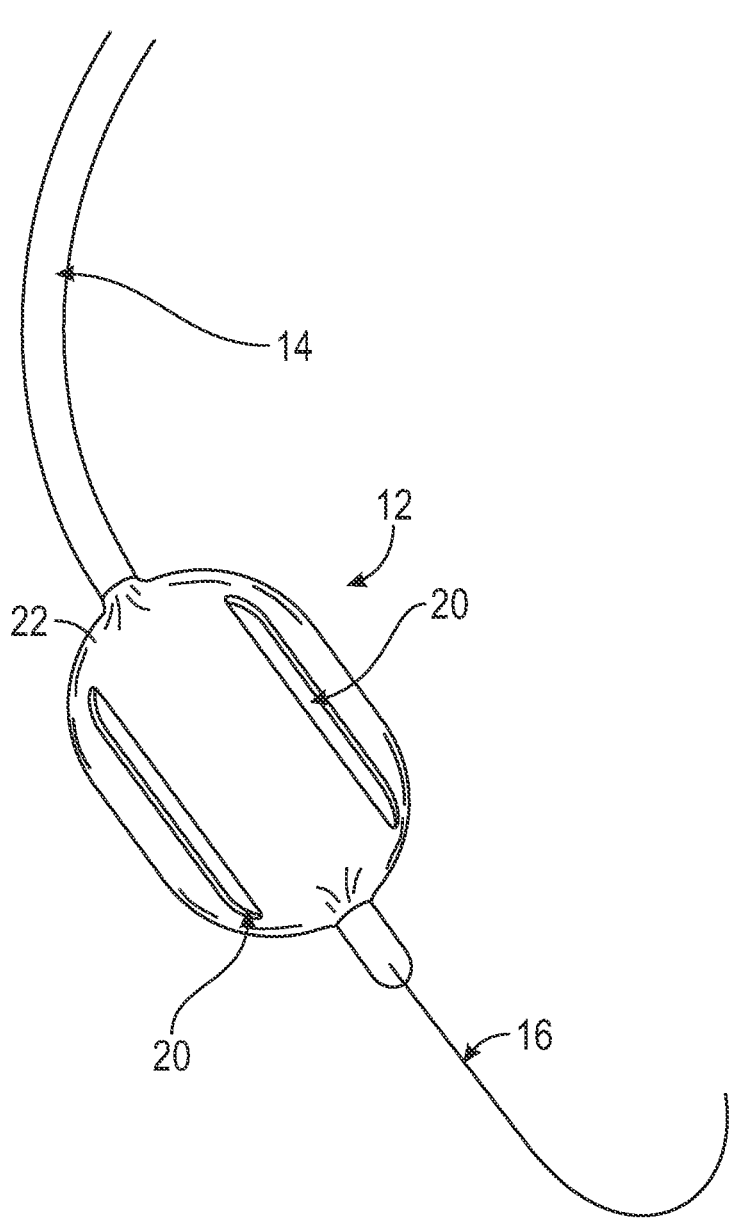
FIG. 6 is a perspective view of a cutting assembly that includes a balloon as the expansion member.

In another preferred embodiment, as shown in FIG. 6, the expansion member is a balloon 22 or other component capable of being delivered through a catheter and then expanded such that the cutting members 20 can cut or dissect the leaflets as further discussed below.

FIG. 1 shows a TAVR heart valve (referred to herein as first replacement valve 100) with leaflets 102 that has been previously placed in the aortic valve of a heart and has now degenerated to the point to which it needs to be replaced by a new TAVR heart valve. This procedure may be referred to herein as valve in valve TAVR). TAVR is short for transcatheter aortic valve replacement. In FIG. 1, the expansion member 18 has been delivered via or through the catheter 14 and expanded or deployed within the first replacement valve 100. The longitudinally extending cutting members 20 are shown extending above and below the frame or stent of the first replacement valve 100. FIG. 1 shows the first replacement valve 100 prior to cutting of the leaflets 102. The expansion member 18 is movable between a delivery position and an expanded position where the leaflets 102 are cut.

In a preferred embodiment, the cutting members 20 can be electrified or may be electrodes that ablate or otherwise affect the leaflet material so as to aid in the cutting, incising or slicing of the leaflets. The cutting members may be actuated to be electrified via controls proximal to the user. In another embodiment, the cutting members 20 may not be electrified. In another embodiment, the cutting members are not sharp enough to cut the leaflets and only slice the leaflets via being electrified. Any type of actuation or electrification for providing cutting is within the scope of the present invention (e.g., radio frequency). The cutting system 10 may include controls for expanding the expansion member 18 and actuating and/or electrifying the cutting members 20 and other necessary controls for control of the system. For example, see button 19 in FIG. 7 that may be used to actuate or electrify the cutting members. If the expansion member is a stent or frame, the expansion member 18 may automatically expand upon removal from the catheter 14 or sheath (e.g., when the catheter is moved proximally to expose the expansion member 18). The expansion member 18 may be made of a shape memory metal mesh. For example, Nitinol

Figure 5:
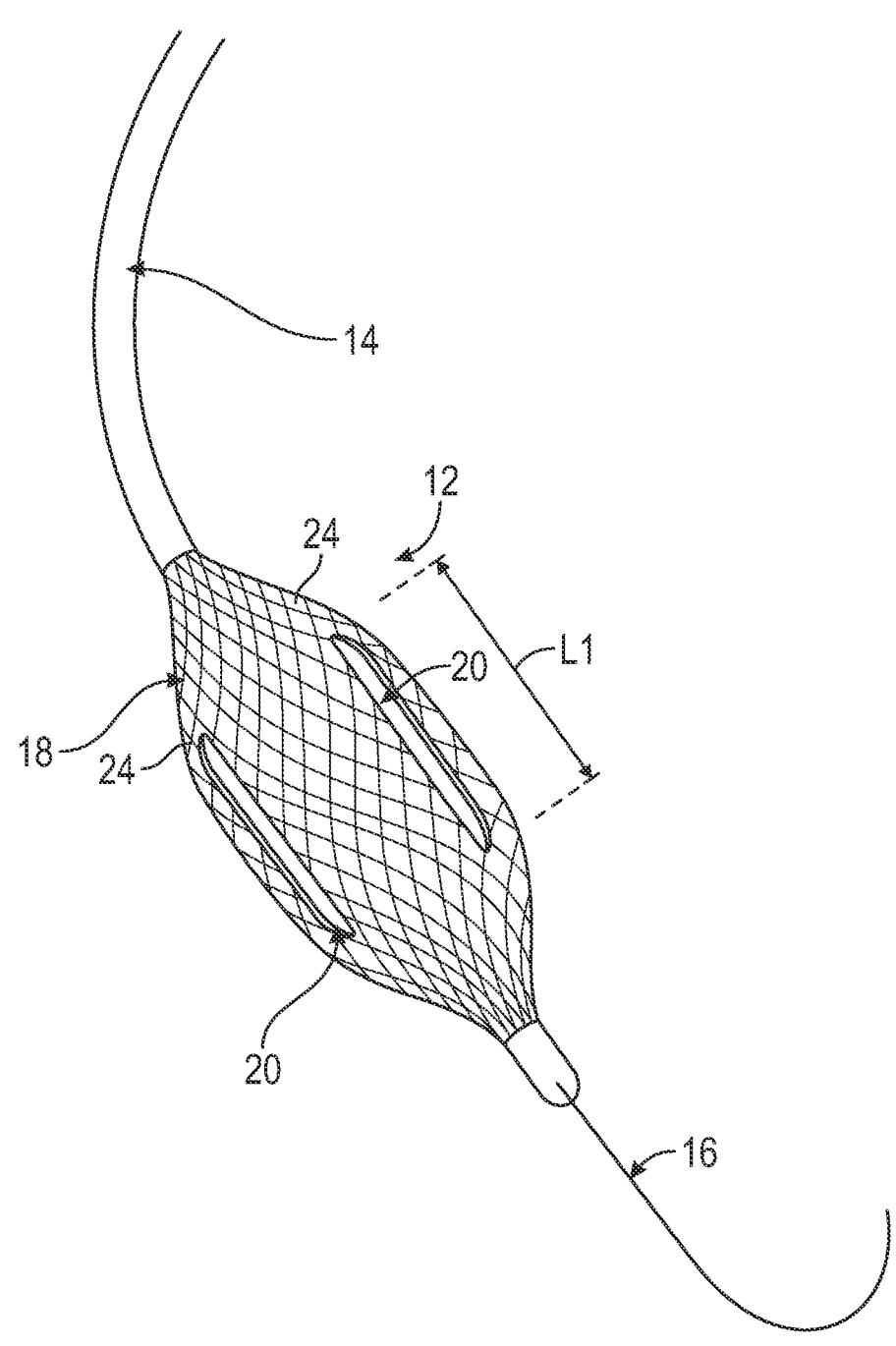
FIG. 5 is a perspective view of the cutting assembly of FIG. 1.

6 is one suitable material. The cutting members 20 are electrically communicated with an electrical source (e.g., a battery or other power source) that may be located outside the body and proximal to the user during use or may be deliverable with the cutting assembly 12. For example, see power cord 21 in FIG. 7. One or more wires may extend to the cutting members or to the expansion member to provide electrical communication. The expansion member 18 may include or provide the wires, filaments or elements that are a portion of the electrical path to the cutting members. The current or other electrical communication may be routed through the frame of the expansion member 18 or a portion thereof and to the cutting members 20. For example, see the wires labeled 24 in FIG. 5 wherein the expansion member 18 is a braid frame and the wires 24 or portion of the braid frame electrically communicate the cutting members 20 with the power source.

Figure 2:
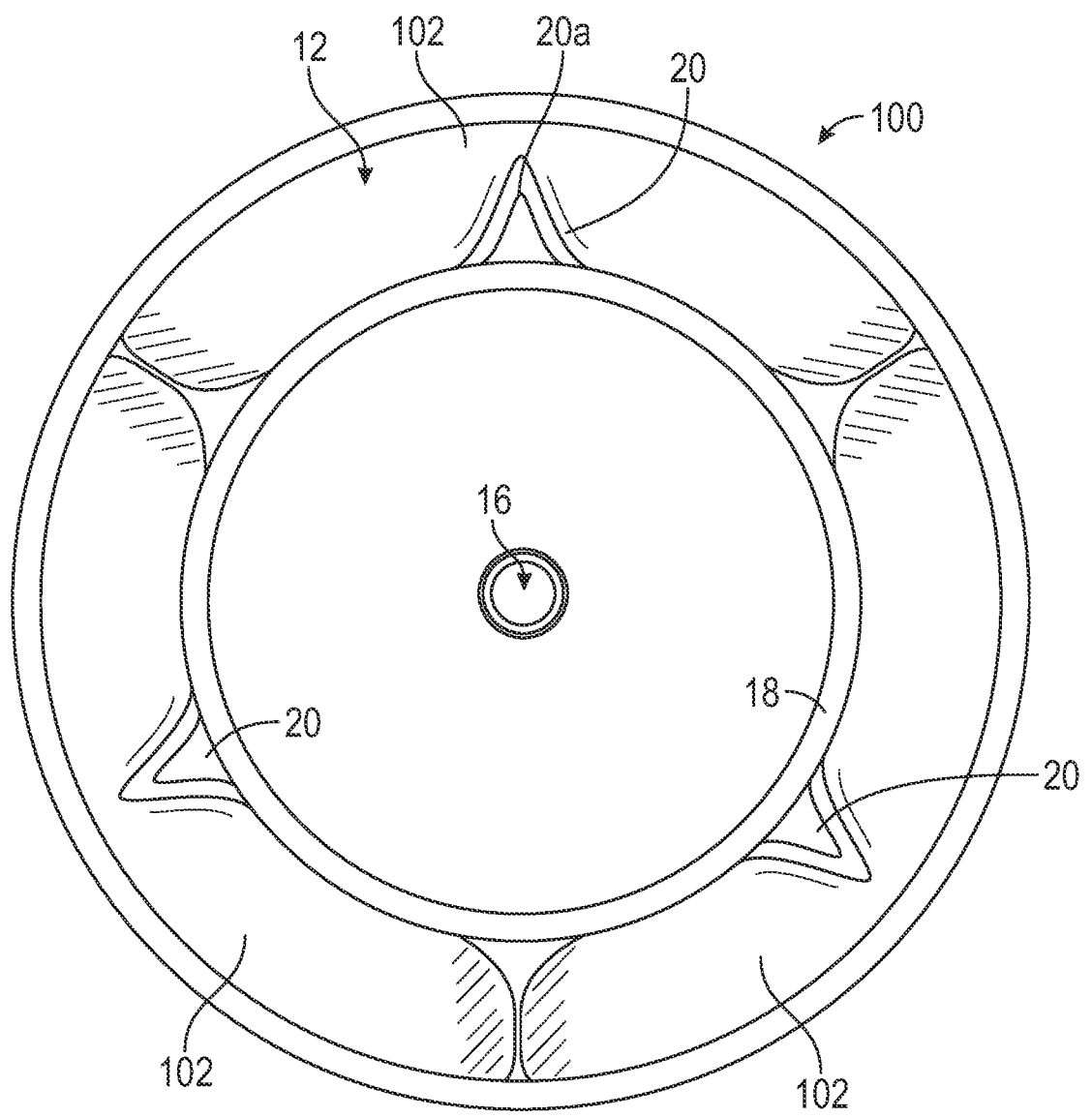
FIG. 2 is a schematic end view of the cutting assembly of FIG. 1 while cutting the leaflets of the first replacement valve.
Figure 3:
FIG. 3 is a perspective view of the cutting assembly of FIG. 1 after the leaflets of the first replacement heart valve have been cut.
Figure 4:
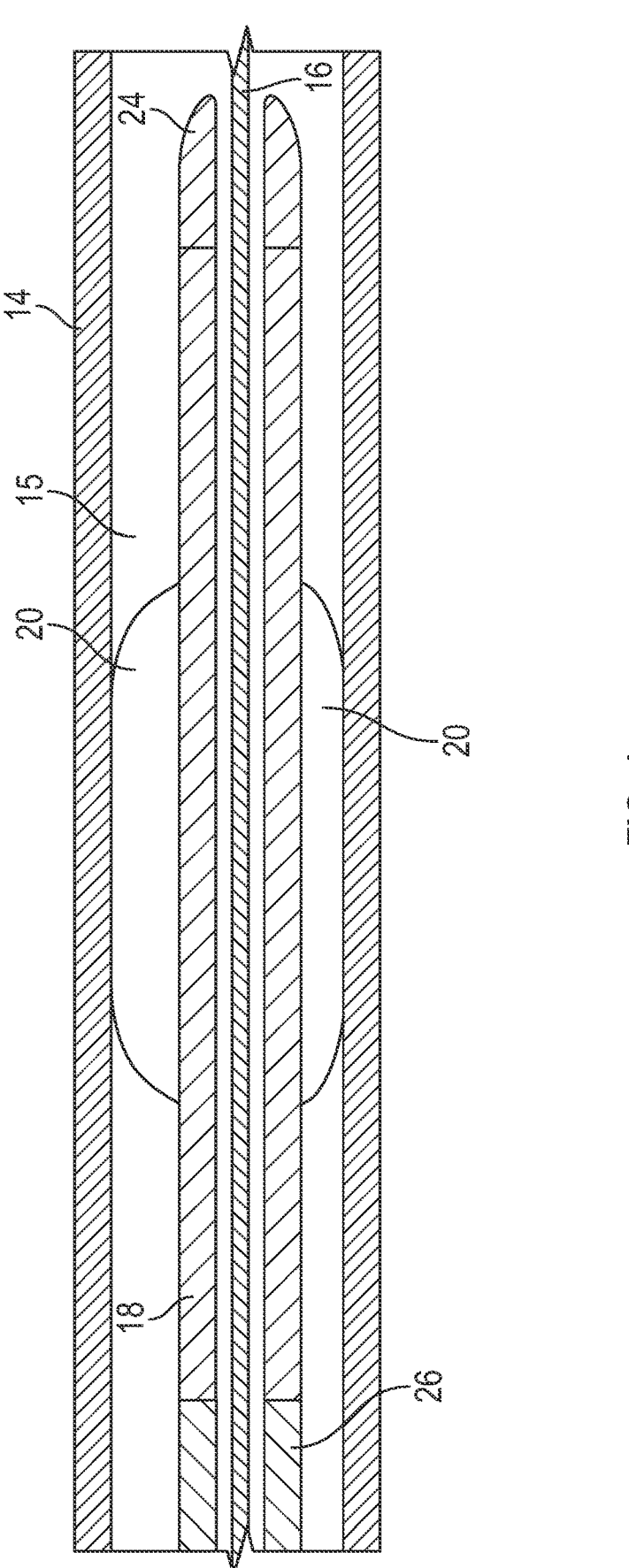
FIG. 4 is a cross-section of the cutting assembly of FIG. 1 in the stowed position and contained within the lumen of the sheath.

FIGS. 2 and 3 show the cutting system 10 during cutting or slicing of the leaflets 102 of the first replacement valve 100. FIG. 2 shows the electrified cutting surface 20a of the blades or cutting members 20 as they are cutting into the leaflets 102 of the first replacement valve 100. In FIG. 3, the leaflets of the first replacement valve 100 extend upwardly beyond the stent or cage 104 and are being incised by the cutting members 20. In other words, the cutting members 20 are longer or have a longer length dimension (cutting member length L1) in a longitudinal or axial direction than the height or length of the leaflets (a leaflet length), entire first replacement valve 100 and/or cage 104. FIG. 3 shows the height or length dimension of the first replacement valve as L2. With the cutting members 20 being this length, the leaflets can be cut via expansion of the expansion member and/or electrification of the cutting member 20 and without the need for axial movement of the cutting members 20. In another embodiment, the assembly can be configured such that the cutting members 20 can be moved axially (proximally and/or distally) to help with cutting of the leaflets. FIG. 3 shows the cage being cut by the cutting members 20, however, this is not a limitation on the present invention and the cutting members may only cut the leaflets.

After the complete incision is made (bisecting or cutting the leaflets 102), the leaflets preferably no longer block the coronary arteries. It will be appreciated that after this procedure has been performed and the cutting assembly 10 is removed back through the catheter, a new or second replacement valve (now shown) can be delivered and deployed inside the remains of the first replacement valve 100. In a procedure where a first replacement heart valve is being inserted in the aortic valve, the cutting assembly 10 can be used to cut, slice or incise the native leaflets prior to deployment of the replacement valve. The cutting system can be used prior to TAVR into a native valve, TAVR into a TAVR valve and TAVR into a replacement valve that was previously implanted surgically.

Figure 7:
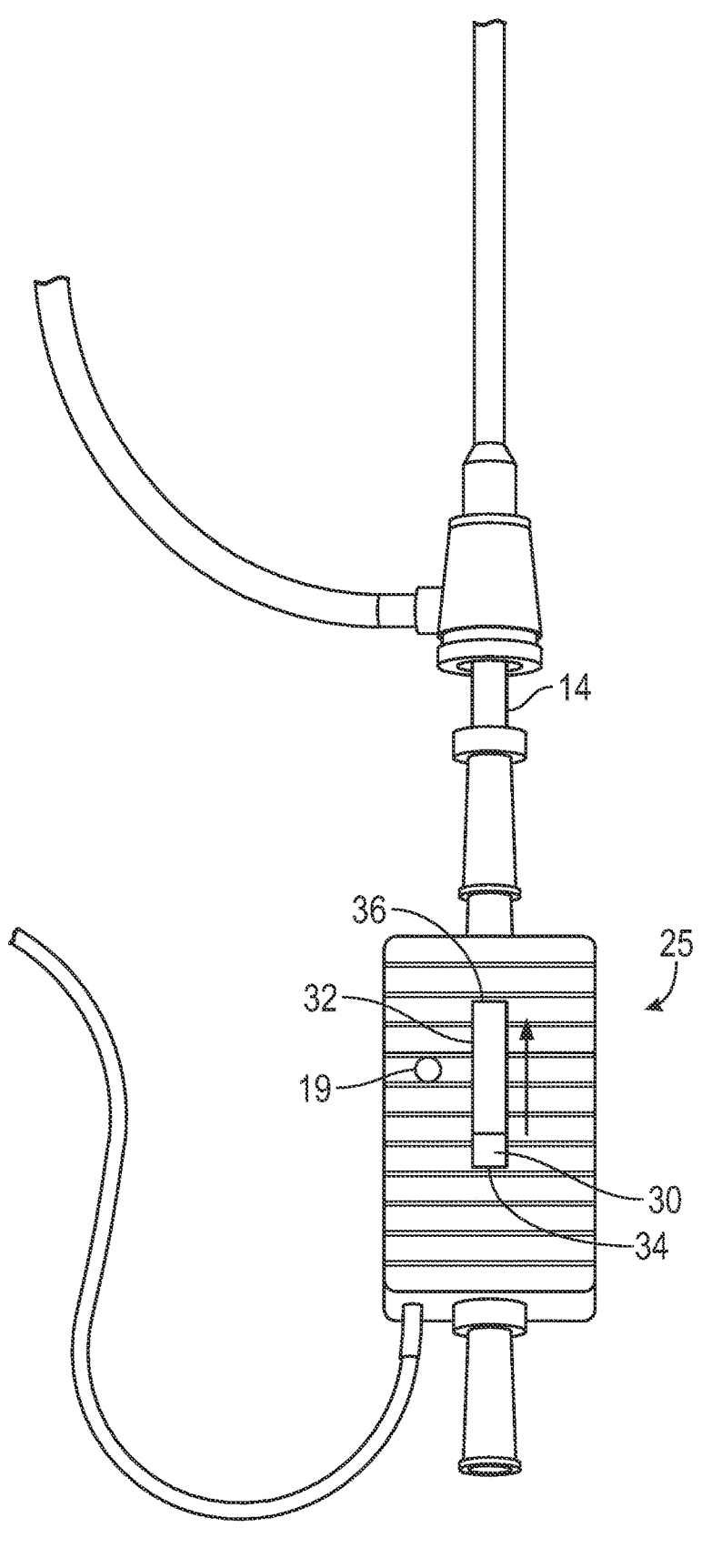
FIG. 7 is a schematic view of the proximal end of the cutting system showing exemplary controls.

In a preferred embodiment, the expansion member 18 may be expandable to an intermediate position where the leaflets 102 are not yet cut and then further expanded to the expanded position, where the leaflets 102 are cut. In this embodiment, as shown in FIG. 7, the cutting system or cutting assembly may include controls 25 for moving or expanding the expansion member 18 between the intermediate position and expanded position. The controls may be any type of controls known for manipulating, articulating or otherwise moving, expanding or affecting frames, stents, balloons or components thereof. For example, the expansion member 18 may be actuated or expanded via pushing or pulling one or more wires, levers, switches, handles or the like.

Figure 8:
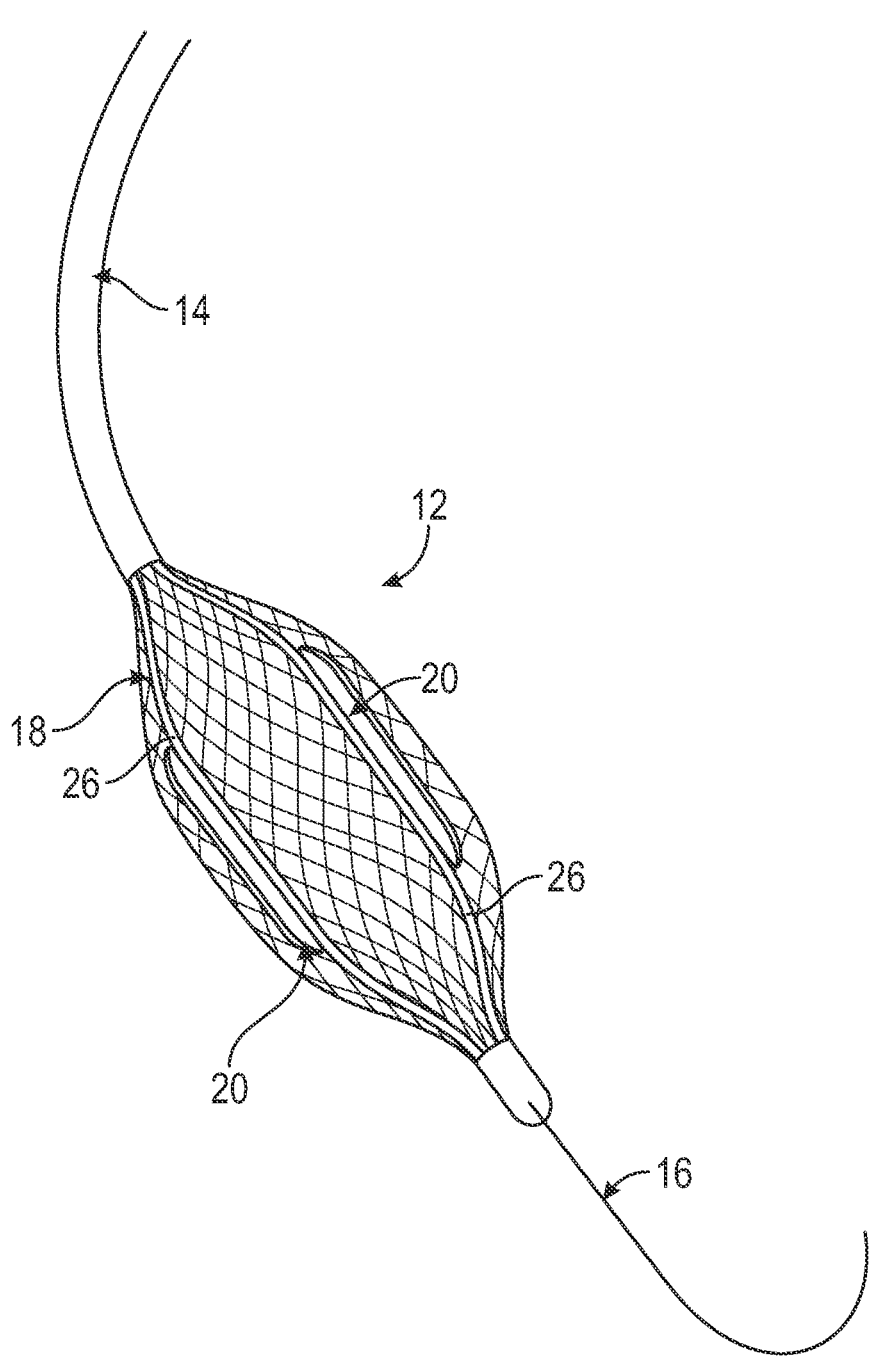
FIG. 8 is a perspective view of a cutting assembly in accordance with another preferred embodiment of the present invention.

As shown in FIG. 8, the expansion member 18 may include arms 26 that are expandable via controls located proximal to the user. The arms 26 and/or the expansion member 18 may be expandable or movable to the expanded position (either from the stowed position or the intermediate position) via a linear switch or switch member 30 that moves forwardly and backwardly to expand the expansion member 18 or the arms 26 thereof between the intermediate position and the expanded position. Movement of the switch member 30 from the first position to the second position expands the expansion member 18 from the intermediate position to the expansion or cutting position. For example, one or more cables, wires, extension members or the like can extend between the switch member and the expansion member and/or arms. In a preferred embodiment, the switch member 30 is movable within a slot 32 that includes a first stop member 34 and a second stop member 36. When the switch member 30 is moved distally (see the arrow in FIG. 7), the second stop member 36 stops the switch member 30, thus preventing the expansion member 18 and the cutting members 20 thereon from moving beyond the expanded position. In a preferred embodiment, the expansion member 18 and/or arms 26 (and the cutting members 20 thereon) are biased from the expanded position back to the intermediate position or the stowed position. The arms 26 may provide the biasing, the expansion member 18 frame and/or the material thereof may provide the biasing or the controls 25 may include a spring or other biasing member therein for biasing the cutting members 20 from the expanded position. In an embodiment where the cutting members 20 are electrified, the cutting system may be configured so that the cutting members 20 are actuated or electrified when the expansion member 18 and/or arms 26 are moved to the expanded position. The arms 26 may be configured to provide the required current or the like to the cutting members.

In another embodiment, the cutting members 20 may be recessed into the frame of the expansion member 18 and can be movable outwardly between a stowed position and a cutting position. In this embodiment, the expansion member 18 may be expand from the stowed position to the expanded position and then the cutting members 20 can be moved, actuated or otherwise deployed to the cutting position. Preferably, the cutting members 20 move laterally or transversely with respect to the axis of the catheter and guide wire.

Figure 9:
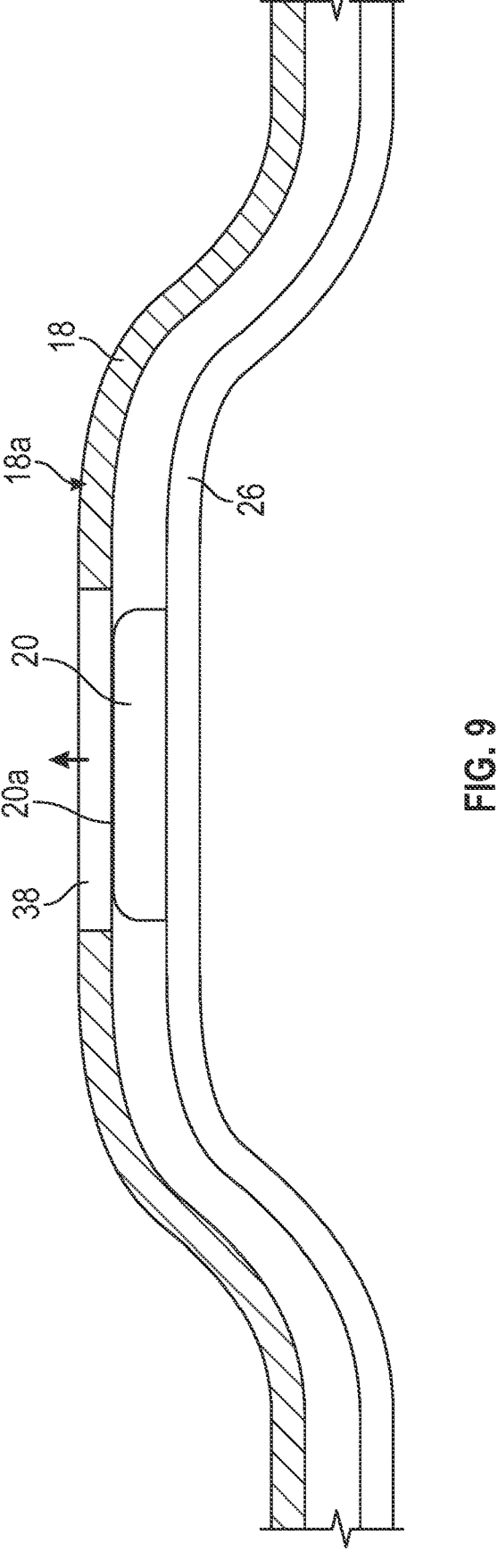
FIG. 9 is a cross-section of a portion of a cutting assembly in accordance with another preferred embodiment of the present invention showing the cutting member positioned inboard of a slot in the expansion member.

As shown in FIG. 9, the cutting members 20 may be movable with respect to the expansion member 18 between a stowed position and a cutting position. The cutting member 20 may be movable with respect to the expansion member 18 and the frame thereof between a stowed position where the outer or cutting edge 20a of the cutting member is located inboard or inside of the outer surface 18a of the expansion member 18 and a cutting position where the cutting edge 20a of the cutting member 18 is located outboard or outside of the outer surface 18a of the expansion member so that it contacts and cuts the leaflet. The cutting members 20 may be mounted on arms 26 that are not integral with the frame of the expansion member 18, but may be located generally within the interior of the expansion member 18 and the cutting members 20 may be movable outwardly through a slot 38 in the expansion member 18 between the stowed position and the cutting position.

Figure 10:
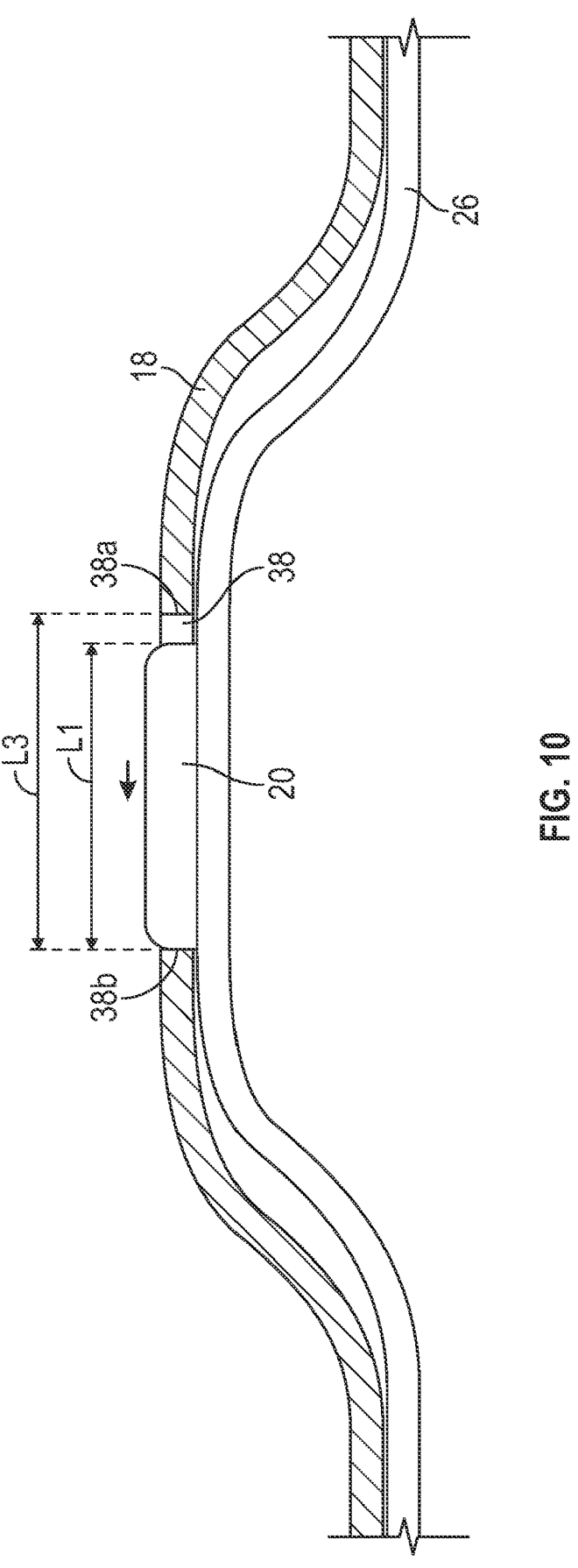
FIG. 10 is a cross-section of a portion of a cutting assembly in accordance with another preferred embodiment of the present invention showing the cutting member positioned with a slot in the expansion member and configured to move axially.

As shown in FIG. 10, the cutting members 20 can also be configured to move axially or longitudinally (generally parallel with the axis of the catheter, expansion member or guide wire) within the slot 38. In this embodiment, each slot 38 has a length (slot length L3) that is longer than the length of the associated cutting member 20. The cutting members may be mounted on an arm or the like and may be actuated via controls proximal to the user between a first cutting position and a second cutting position to provide a cutting or slicing motion. For example, one or more wires, cables, extension members or components that extend to or are otherwise associated with the arms 26, expansion member 18, cutting members 20, inner expansion member or other component operatively connected to or associated with the cutting members may be pushed or pulled to provide the axial movement. In this embodiment, the ends or end surfaces of the slot may act as stop members (see first and second stop surfaces 38a and 38b in FIG. 10) to provide a defined length of the movement provided by the cutting members 20. In use, the cutting members 20 can be moved from the first cutting position to the second cutting position or can be moved back and forth between the first and second cutting positions to provide the desired cutting of the leaflets. The cutting members 20 may be electrified simultaneously to the cutting motion. It will be appreciated that the cutting members 20 can be electrified in any embodiment discussed herein and that any of the features discussed in any one embodiment are interchangeable with the features of any other embodiment.

In another embodiment, the cutting edges may be located outboard of the outer surface 18a in the non-cutting position, but move further outwardly to the cutting position. Any method or configuration for moving the cutting members 20 independently of the expansion member 18 or frame is within the scope of the present invention. In this embodiment, the expansion member may expand from the stowed position to the expanded position upon exiting the sheath and then the cutting members can be moved from the first or non-cutting position to the second or cutting position. The arms can be made of a shape memory alloy. The outer surface 18a of the expansion member 18 may hold the leaflets in a desired position after moving from the stowed position to the expanded position, and the cutting members 20 then incise the leaflets. The surface area of the outer surface 18a of the expansion member is greater than the surface area of the adjacent inner surface of the leaflets 102. This allows the expansion member 18 to secure the leaflets in position so that they can be cut by the cutting members 20. The cutting members 20 may also be mounted on an inner expansion member and/or braid frame that is expanded separately from expansion member 18. The arms 26 or other component operatively connecting the cutting members 20 with the controls for moving the cutting members between first and second positions may also be integral with the expansion member 18 (e.g., they may be woven or extended through the braid frame). The arms 26 (and the cutting members 20 thereon) may also be positioned outboard or outside of the expansion member 18 and moveable with respect to the expansion member 18.

The cutting members may each be located on a levered or pivotable arm that is biased to the cutting position. In this embodiment, the arm is held in the non-cutting position and when released the free end of the arm and the cutting members spring, move or are biased to the cutting position. In another embodiment, the cutting members may be oriented or configured in a helical configuration or a configuration where they extend laterally or generally perpendicular to the axis of the catheter. The expansion member and/or the cutting members can be configured to spin or spiral about the axis of the guide wire.

In another embodiment, the cutting system may include an embolic protection device, such as that disclosed in U.S. Patent Publication No. 2021/0145561, the entirety of which is incorporated by reference herein. The embolic protection device can prevent any portions or pieces of the valve, leaflets or other components or embolic material from entering the coronary arteries.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A cutting system for use prior to valve replacement, the cutting system comprising:

a cutting assembly that includes an expansion member that is movable between a stowed position and an expanded position, wherein the expansion member includes a slot defined therein, at least a first cutting member associated with the expansion member, wherein the first cutting member is movable radially outwardly with respect to the expansion member between a non-cutting position and a cutting position, wherein in the non-cutting position a cutting edge of the cutting member is located inboard of an outer surface of the expansion member and in the cutting position the cutting edge is located outboard of the outer surface of the expansion member, when the expansion member is in the expanded position, the first cutting member is movable radially outwardly through the slot between the non-cutting position and the cutting position, such that the cutting edge is located outboard of the outer surface of the expansion member, and when the expansion member is in the expanded position, the first cutting member is movable axially within the slot between a first cutting position and a second cutting position when the cutting edge is located outboard of the outer surface of the expansion member, and a sheath that defines a lumen therethrough, wherein the cutting assembly is movable within the lumen.

2. The cutting system of claim 1 wherein the expansion member is an expandable balloon.

3. The cutting system of claim 1 wherein the first cutting member includes an actuated state in which the first cutting member is electrified.

4. The cutting system of claim 3 wherein the expansion member is a braid frame, and wherein a portion of the braid frame electrically communicates the first cutting member with a power source.

5. The cutting system of claim 1 wherein the expansion member is an expandable braid frame that is biased to the expanded position.

6. The cutting system of claim 1 wherein the cutting assembly includes second and third cutting members associated with the expansion member, wherein the second and third cutting members are configured to incise second and third leaflets, respectively.

7. The cutting system of claim 6 wherein the first, second and third cutting members define a length dimension, and wherein the length dimension is greater than a leaflet length.

8. The cutting system of claim 1 wherein the expansion member is expandable radially outwardly from the stowed position to an intermediate position and from the intermediate position to the expanded position.

9. The cutting system of claim 8 further comprising a switch member, wherein the switch member is configured to move the expansion member from the intermediate position to the expanded position.

10. The cutting system of claim 9 wherein the switch member is movable between a first position and a second position, wherein movement of the switch member from the first position to the second position moves the expansion member from the intermediate position to the expanded position.

11. The cutting system of claim 1 wherein the slot defines a slot length and the first cutting member defines a cutting member length, wherein the slot length is longer than the first cutting member length.

12. The cutting system of claim 11 wherein the slot includes first and second stop surfaces, wherein in the second cutting position the first cutting member contacts the second stop surface.

13. The cutting system of claim 1 wherein the expansion member is a braid frame, wherein the first cutting member is mounted on an arm, and wherein the arm and first cutting member are movable axially with respect to the braid frame when the expansion member is in the expanded position.

14. The cutting system of claim 13 wherein the arm is biased from the expanded position back to an intermediate position.

15. The cutting system of claim 1 wherein the first cutting member is mounted on an inner expansion member that is expandable separately from the expansion member.

*    *    *    *    *